(12) United States Patent
Yeung et al.

(10) Patent No.: US 7,699,819 B2
(45) Date of Patent: Apr. 20, 2010

(54) MOLECULAR SIEVE AND ZEOLITE MICRONEEDLES AND PREPARATION THEREOF

(75) Inventors: King Lun Yeung, Hong Kong (HK); Ling Wai Wong, Hong Kong (HK); Wenqing Sun, Shanghai (CN); Wai Kin Leung, Hong Kong (HK); Wing Yan Lai, Hong Kong (HK); Ngar Wai Chan, Hong Kong (HK)

(73) Assignee: The Hong Kong University of Science and Technology, Kowloon, Hong Kong (CN)

( * ) Notice: Subject to any disclaimer, the term of this patent is extended or adjusted under 35 U.S.C. 154(b) by 689 days.

(21) Appl. No.: 11/674,881

(22) Filed: Feb. 14, 2007

(65) Prior Publication Data

US 2007/0280878 A1    Dec. 6, 2007

Related U.S. Application Data

(60) Provisional application No. 60/776,107, filed on Feb. 21, 2006.

(51) Int. Cl.
*A61F 13/00* (2006.01)
*C01B 39/02* (2006.01)
*B28B 1/30* (2006.01)

(52) U.S. Cl. .................. 604/272; 604/191; 423/701; 423/709; 424/449; 264/225; 264/306

(58) Field of Classification Search ................ 423/701, 423/709; 604/191, 272; 424/449; 264/225, 264/306
See application file for complete search history.

(56) References Cited

U.S. PATENT DOCUMENTS

| | | | |
|---|---|---|---|
| 5,591,139 A | 1/1997 | Lin et al. |
| 5,855,801 A | 1/1999 | Lin et al. |
| 6,334,856 B1 | 1/2002 | Allen et al. |
| 6,503,231 B1 | 1/2003 | Prausnitz et al. |
| 6,611,707 B1 | 8/2003 | Prausnitz et al. |
| 6,743,211 B1 | 6/2004 | Prausnitz et al. |
| 6,881,203 B2 | 4/2005 | Delmore et al. |
| 6,908,453 B2 | 6/2005 | Fleming et al. |
| 6,924,087 B2 | 8/2005 | Yeshurun et al. |
| 7,048,723 B1 | 5/2006 | Frazier et al. |
| 7,226,439 B2 | 6/2007 | Prausnitz et al. |
| 7,344,499 B1 | 3/2008 | Prausnitz et al. |
| 2002/0082543 A1 | 6/2002 | Park et al. |
| 2002/0193754 A1 | 12/2002 | Cho |
| 2003/0111759 A1 | 6/2003 | Wood et al. |
| 2003/0135167 A1 | 7/2003 | Gonnelli |
| 2004/0072105 A1 | 4/2004 | Yeshurun et al. |
| 2004/0146611 A1 | 7/2004 | Arias et al. |
| 2004/0186419 A1 | 9/2004 | Cho |
| 2004/0243063 A1 | 12/2004 | Roy et al. |
| 2005/0029223 A1 | 2/2005 | Yeshurun et al. |
| 2005/0137525 A1 | 6/2005 | Wang et al. |
| 2005/0137531 A1 | 6/2005 | Prausnitz et al. |
| 2005/0143713 A1 | 6/2005 | Delmore et al. |
| 2005/0171480 A1 | 8/2005 | Mukerjee et al. |
| 2005/0178760 A1 | 8/2005 | Chang et al. |
| 2005/0187521 A1 | 8/2005 | Fleming et al. |
| 2005/0261631 A1 | 11/2005 | Clarke et al. |
| 2006/0015061 A1 | 1/2006 | Kuo et al. |
| 2006/0025717 A1 | 2/2006 | Zimmermann et al. |
| 2006/0030812 A1 | 2/2006 | Golubovic-Liakopoulos et al. |
| 2006/0086689 A1 | 4/2006 | Raju |
| 2007/0225675 A1 | 9/2007 | Robinson et al. |
| 2007/0260201 A1 | 11/2007 | Prausnitz et al. |
| 2008/0027384 A1 | 1/2008 | Wang et al. |
| 2008/0051699 A1 | 2/2008 | Choi et al. |
| 2008/0269666 A1 | 10/2008 | Wang et al. |
| 2009/0131905 A1 | 5/2009 | Allen et al. |

FOREIGN PATENT DOCUMENTS

| | | |
|---|---|---|
| EP | 1652551 | 5/2006 |
| WO | WO/02/064193 | 8/2002 |
| WO | WO/2005/009645 | 2/2005 |
| WO | WO/2005/044364 | 5/2005 |
| WO | WO/2005/082593 | 9/2005 |
| WO | WO/2006/018642 | 2/2006 |
| WO | WO/2007/127976 | 1/2008 |
| WO | WO/2008/011625 | 1/2008 |

OTHER PUBLICATIONS

Sun, "Thesis", The Hong Kong University of Science and Teachnology Institutional Repository, Http://hdl.handle.net/1783.1/5905, (May 2009).*

Wong, "Thesis",The Hong Kong University of Science and Teachnology Institutional Repository, Http://hdl.handle.net/1783.1/2800, (Mar. 2007).*

Mirfendereski et al, "Probabilistic Response of Micro-Fabricated Polysilicon Beam Structures: Comparison of Analysis and Experiments," ASME Winter Annual Meeting, Proc. ASME, DSC—vol. 46, pp. 77-80, 1993.

Lebouitz, "MEMS Microshells for Microneedles, Microscale Fluid Visualization, and Vacuum Packaging of Microdevices," Ph.D. Thesis, University of California, Berkeley, CA., pp. 1-156, 170 pages total, 1998.

McAllister et al, "Three-Dimensional Hollow Microneedle and Microtube Arrays," Proceedings 10th International Conference on Solid State Sensors and Actuators, pp. 1098-1101, 1999.

(Continued)

*Primary Examiner*—David M Brunsman
(74) *Attorney, Agent, or Firm*—George G. Wang; Wilkinson & Grist

(57) ABSTRACT

A method of making zeolite microneedles includes providing a polymer microneedles template, depositing zeolite seeds on the polymer microneedles template, and growing the zeolite seeds into an array of zeolite microneedles.

25 Claims, 11 Drawing Sheets

OTHER PUBLICATIONS

Stoeber et al, "Fluid Injection Through Out-of-Plane Microneedles", Proceedings of the 1st IEEE-EMBS Special Topic Conference on Microtechnologies in Medicine & Biology, pp. 224-228, 2000.

Brazzle et al, "Micromachined Needle Arrays for Drug Delivery or Fluid Extraction," IEEE Engineering in Medicine and Biology Magazine, 18, (No. 6), pp. 53-58, 1999.

McAllister et al, "Microfabricated microneedles for gene and drug delivery," *Annu. Rev. Biomed. Eng.* 2, pp. 289-313, 2000.

McAllister et al, Microfabricated needles for transdermal delivery of macromolecules and nanoparticles: Fabrication methods and transport studies, *PNAS*, vol. 100, No. 24, pp. 13755-13760, 2003.

Sparks et al, "Micromachined needles and lancets with design adjustable bevel angles," J. Micromech. Microeng. 14, pp. 1230-1233, 2004.

BioValve Technologies, Inc., Company and product information, available at: http://www.biovalve.com/, 13 pages, printed 2007.

Micronit Microfluidics BV, Company and product information, available at: http://www.micronit.com/, 14 pages, printed 2007.

\* cited by examiner

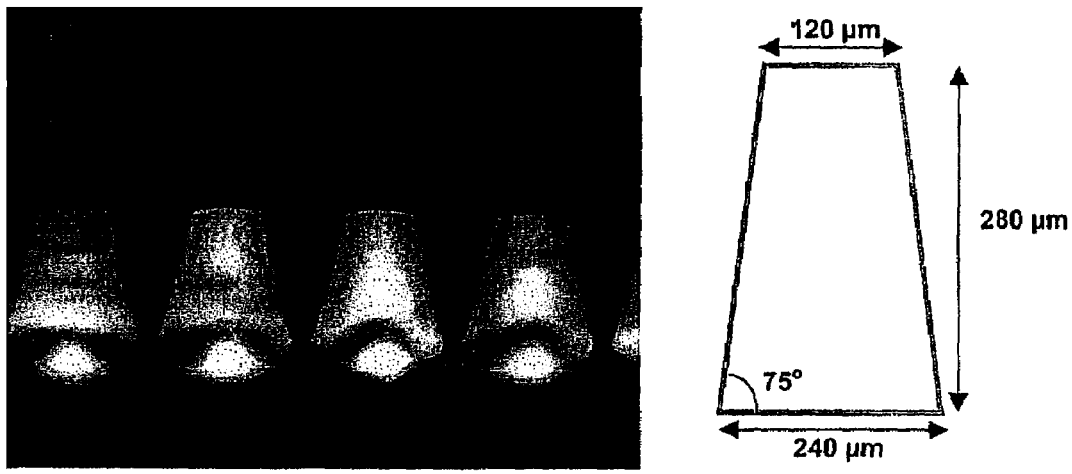
FIG. 2 A fluorescent micrograph and schematic diagram of tapered SU-8 polymer microneedles template.
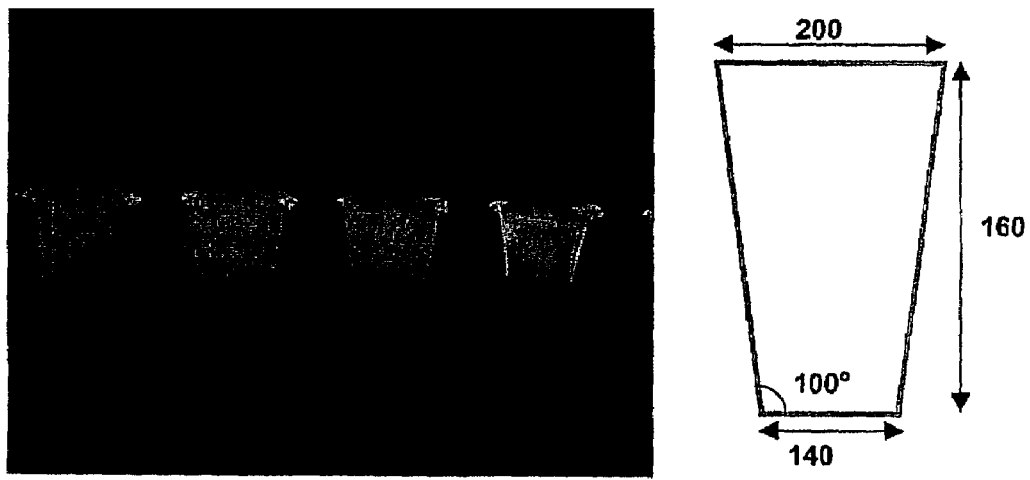
FIG. 3 A fluorescent micrograph and schematic diagram of bowl shaped SU-8 polymer microneedles template.

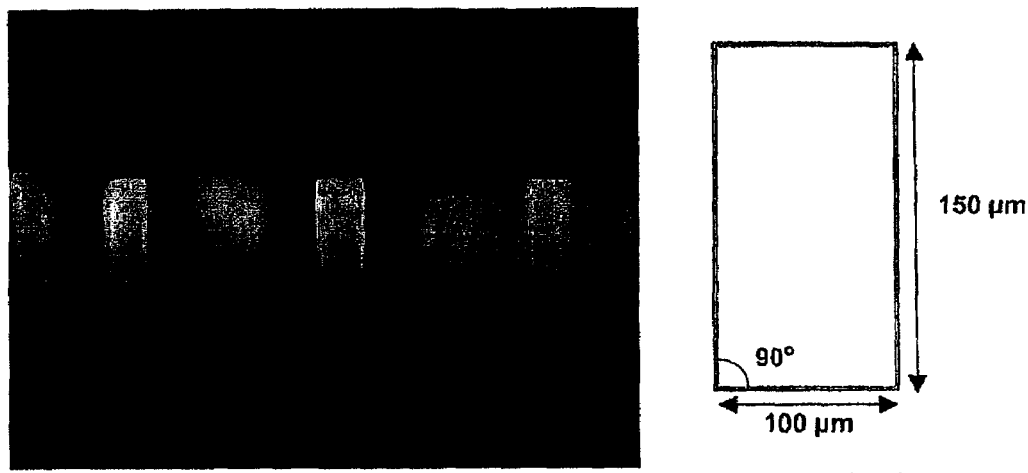
FIG. 4 A fluorescent micrograph and schematic diagram of cylinder SU-8 polymer microneedles template.
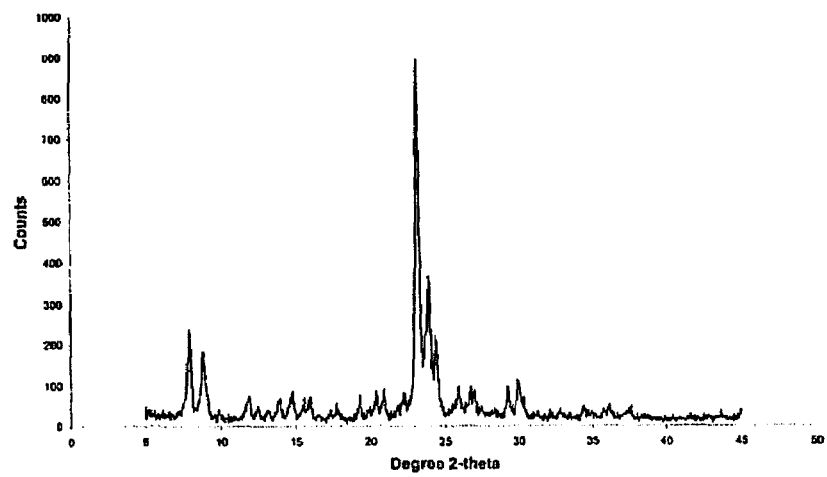
FIG. 5 X-Ray Diffraction pattern (XRD) of silicate 1 seeds.
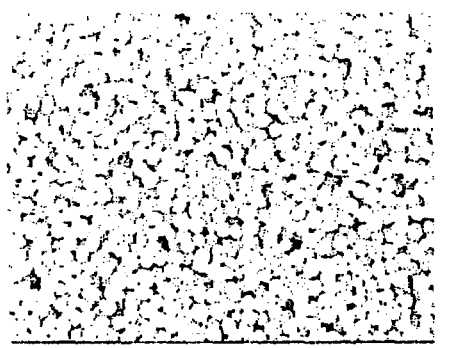
FIG. 6 SEM picture of silicate 1 seeds.

FIG. 7 SEM pictures of zeolite coated microneedle using electrostatic method.

FIG. 8 SEM picture of zeolite microneedles with a shell thickness of 1 μm.

FIG. 9 SEM picture of zeolite microneedles with a shell thickness of 6 μm.

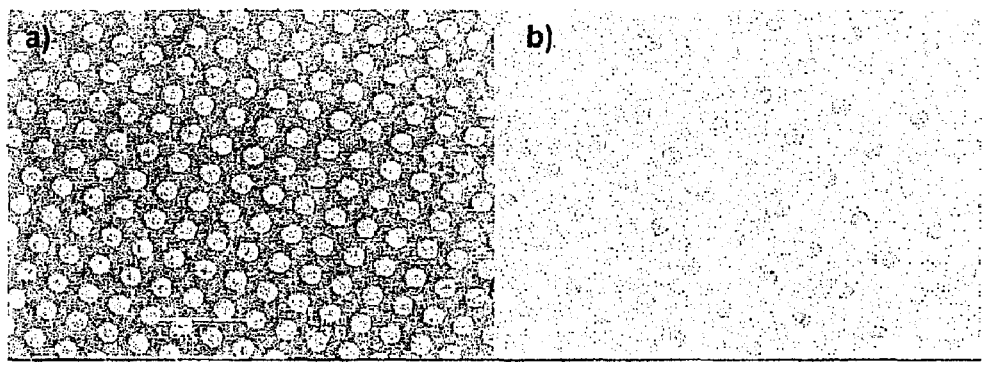
FIG. 10 Electron micrographs of a) closed and b) opened tip microneedles.
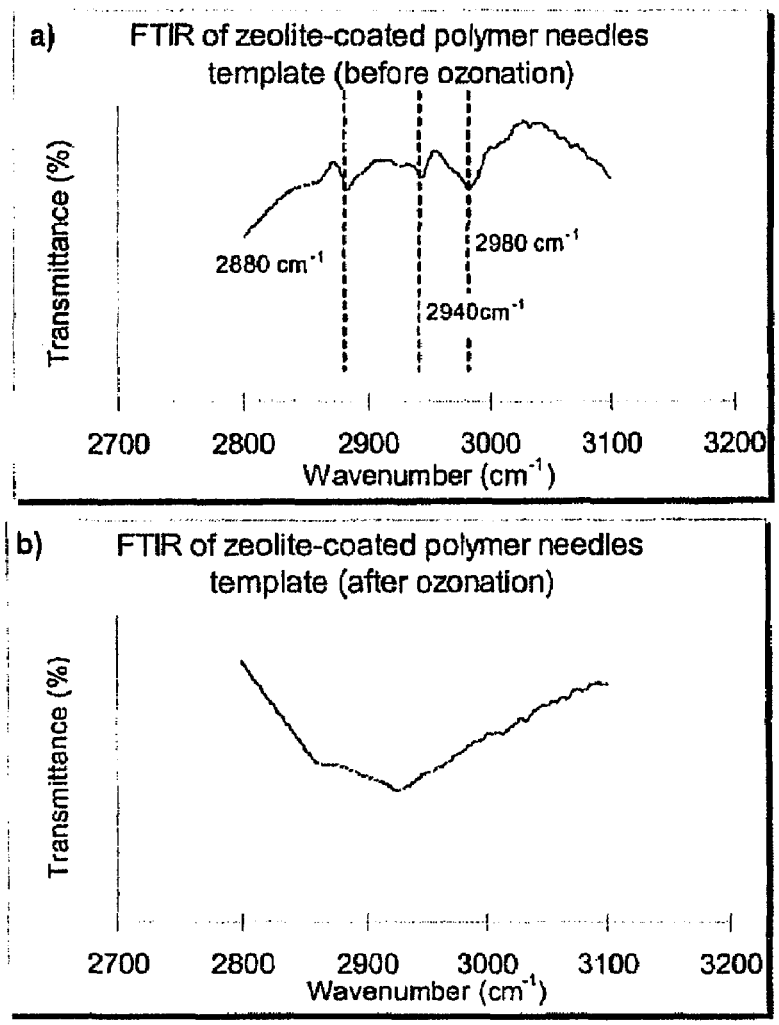
FIG. 11 FTIR analysis of zeolite-coated polymer microneedles template (a) before ozonation (b) after ozonation

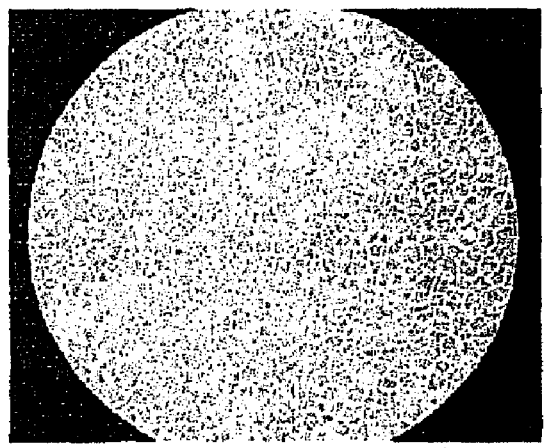
FIG. 12 Control experiment without the addition of zeolite
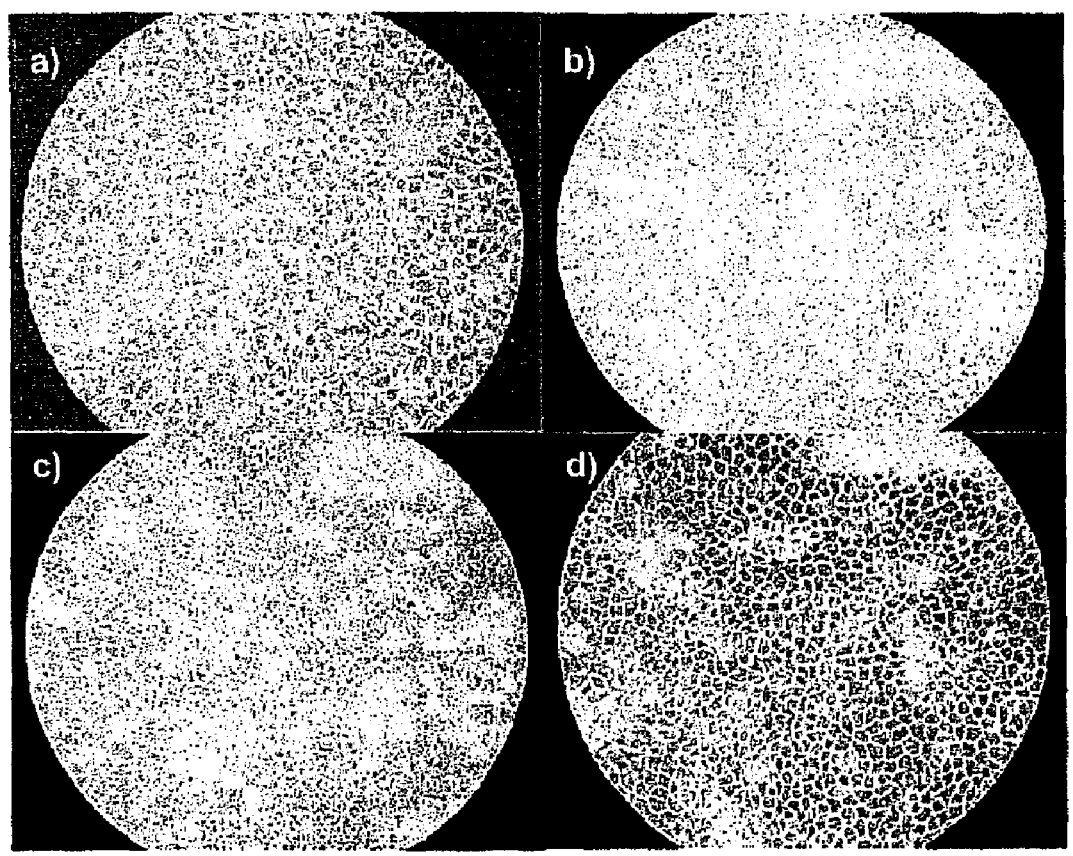
FIG. 13 With the addition of zeolite in the cell culture
    a) Day 0—addition of zeolite
    b) Day 1—incubation of zeolite for 1 day
    c) Day 2—incubation of zeolite for 2 days
    d) Day 3—incubation of zeolite for 3 days

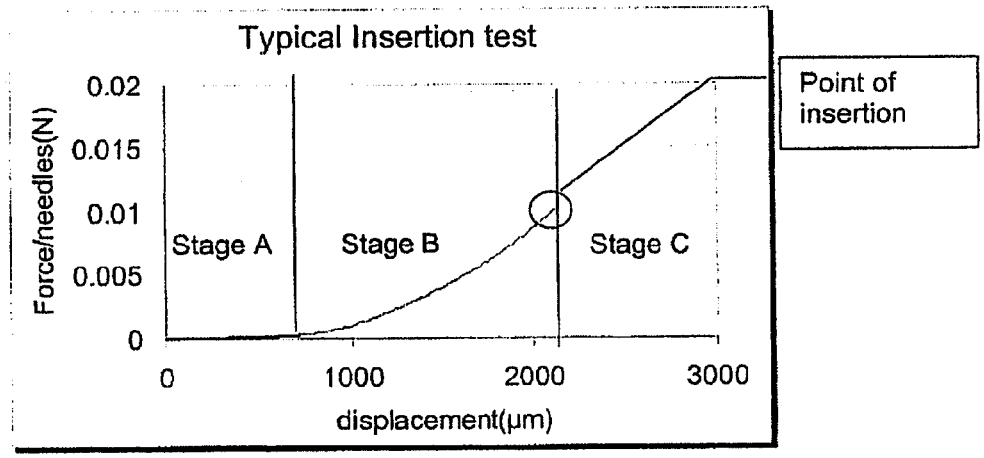
FIG. 14 Force-displacement plot for the insertion of microneedles into a pig's skin
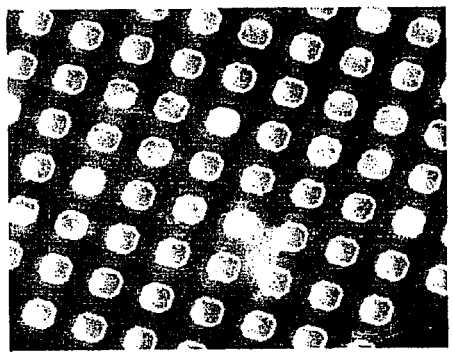
FIG. 15 Optical micrograph of zeolite microneedles after insertion test
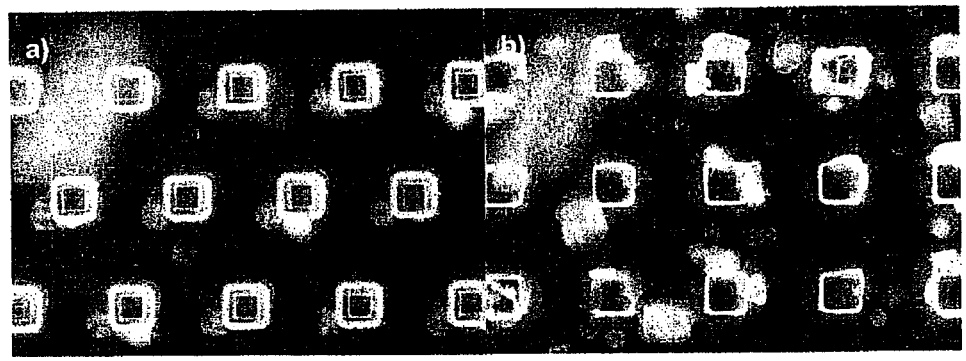
FIG. 16 Microneedles with different packing geometry a) close-packed pattern b) square pattern

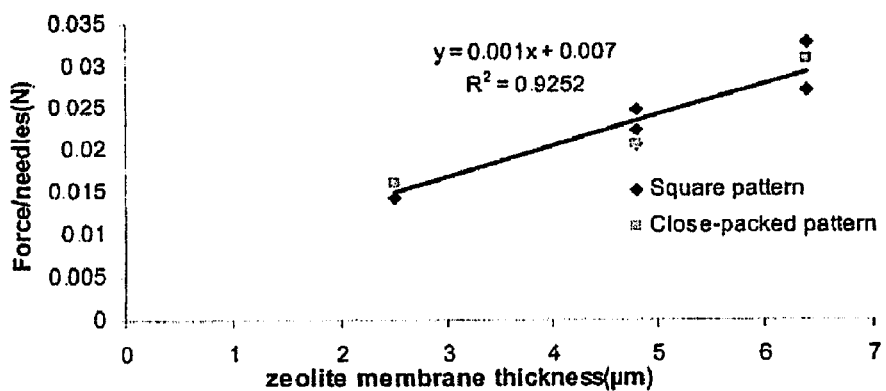
FIG. 17 Insertion force for different thicknesses of zeolite membrane and different packing geometries of microneedles
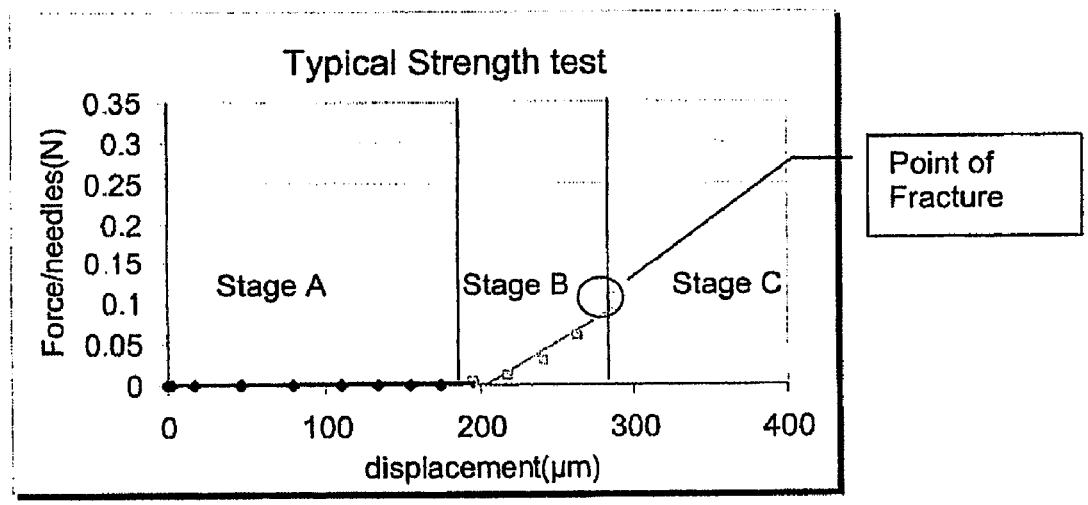
FIG. 18 Force-displacement plot for the strength test of zeolite microneedles

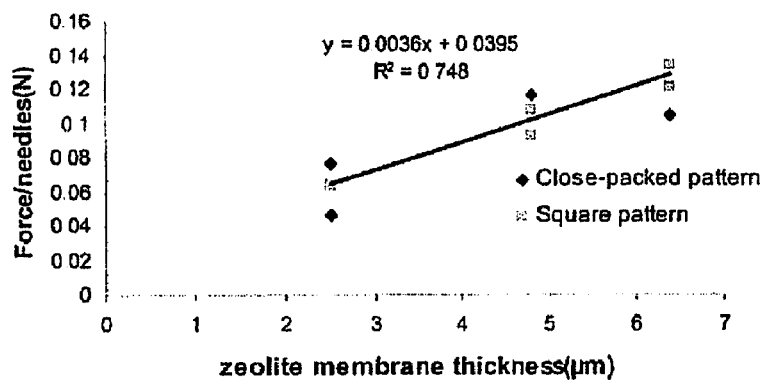
FIG. 19 Force required for the breakage of microneedles for different wall thicknesses of zeolite microneedles and different packing geometries
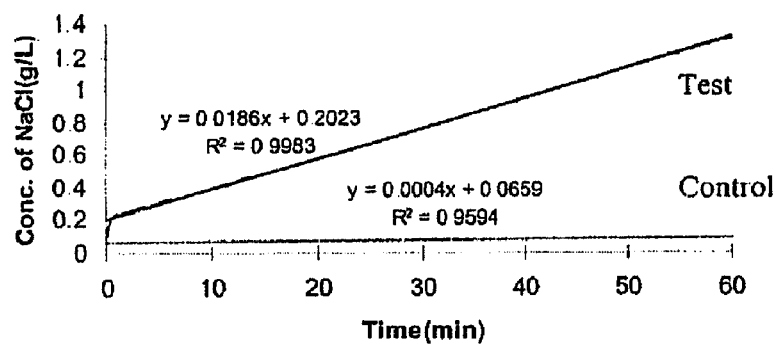
FIG. 20 Change of concentration of sodium chloride in the lower chamber of the diffusion cell

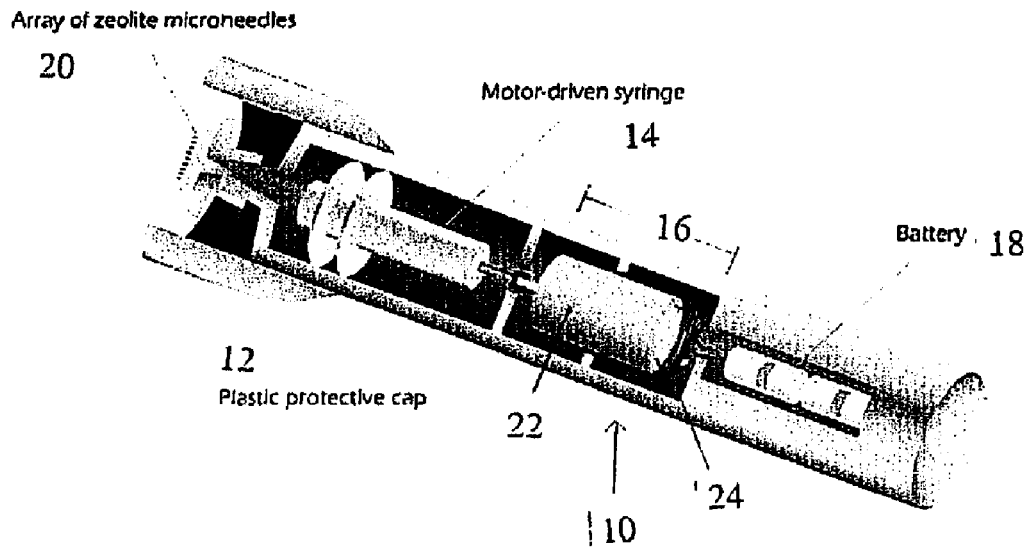
FIG. 21 Internal design of the microneedles pen applicator
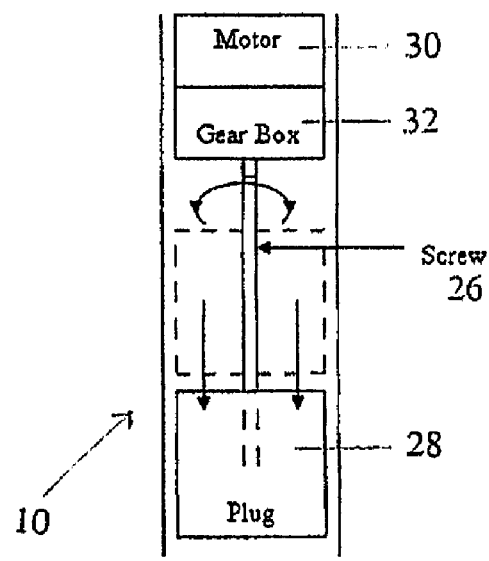
FIG. 22 The mechanical system of the microneedles pen applicator

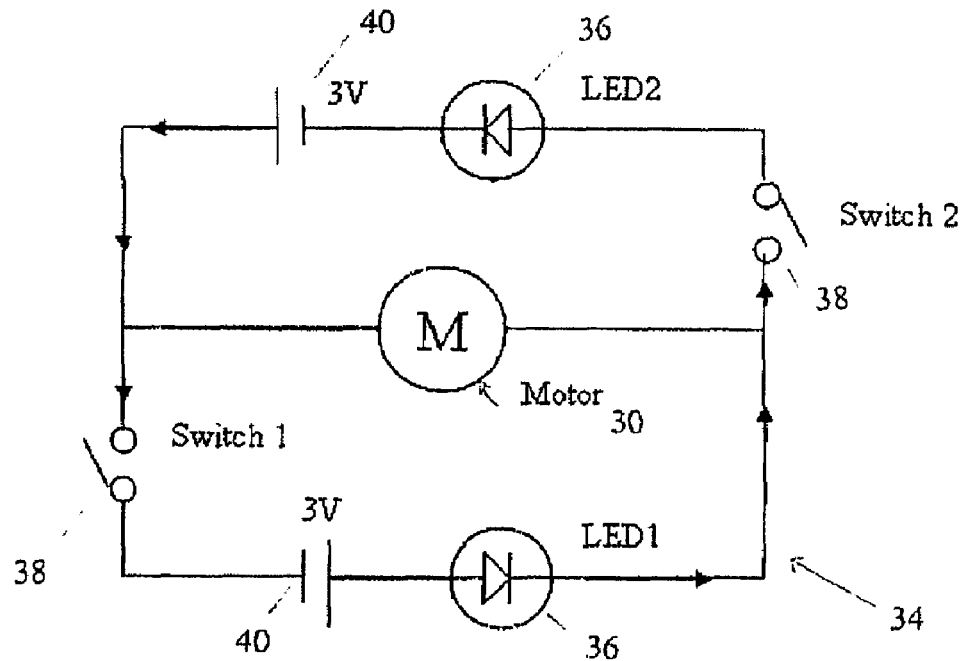
FIG. 23 The electronic circuit design of the microneedles pen applicator
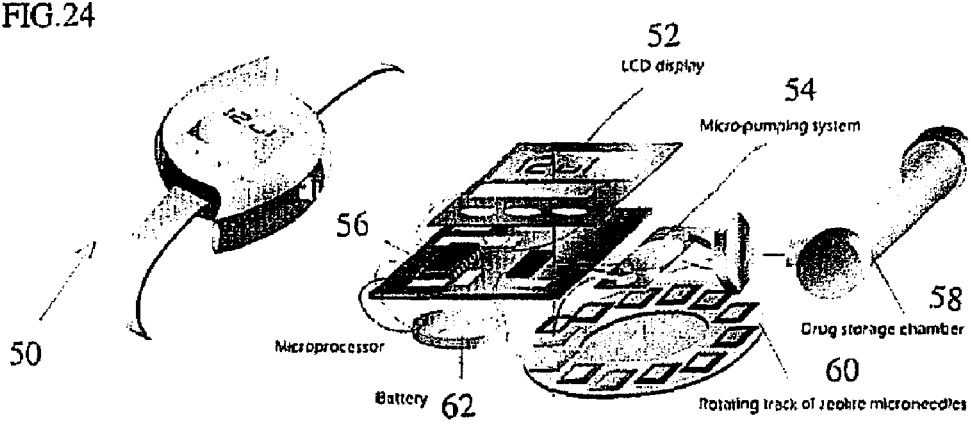
FIG. 25 The conceptual design of microneedles wrist watch applicator

MOLECULAR SIEVE AND ZEOLITE MICRONEEDLES AND PREPARATION THEREOF

The present application claims priority to provisional application No. 60/776,107 entitled "Molecular Sieve and Zeolite Microneedles and Preparation Thereof," that was filed on Feb. 21, 2006, the content of which is incorporated herein by reference.

BACKGROUND

Microneedles are considered a hybrid of hypodermic needles and transdermal patches that involve narrow and shallow injections to administer drugs. Microneedles are a new drug delivery system for transdermal delivery of drug, by virtue of their small dimensions, ability to penetrate into skin tissue in a non-invasive manner and their minimization of the risk for infection. Microneedles typically are around 100-200 microns in length, which is long enough to penetrate the stratum corneum skin barrier but not deep enough to reach the nerves in the dermis layer. Therefore, microneedles may provide a painless injection and may allow patients to operate the microneedles safely on their own.

Microneedles are conventionally made of silicon, glass, metallic material or polymer. Early microneedles were made of silicon and were prepared by microlithography and etching technologies originally developed for the microelectronics industry. Glass microneedles are made using conventional drawn glass micropipette techniques. However, the fragile nature of silicon and glass often results in easy breakage of the microneedles.

Metallic materials, including steel, stainless steel and nickel, may be electrodeposited onto polymeric mold to create microneedles with good mechanical strength. However, the possible toxicity of metals to the human body can limit its area of application and can pose a problem for the waste disposal. Polymeric microneedles are easy to manufacture, safe and inexpensive. A number of biodegradable polymers have been approved by the U.S Food and Drug Administrative (FDA). For example, Poly(lactic-acid) (PLA), poly(glycolic-acid) (PGA) and their copolymers have been used routinely for a narrow range of medical applications. However, the relative low Young's modulus of polymers means the polymer microneedles may not be strong enough to penetrate the skin.

Consequently, it is desirable to develop microneedles with improved properties. Particularly, it is desirable to develop microneedles that exhibit improved mechanical properties and possess improved thermal and chemical stability compared to silicon and polymer microneedles. It is also desirable to develop microneedles that are biocompatible, especially when compared to metal microneedles. Furthermore, it is desirable to develop microneedles that can be produced conveniently and inexpensively.

SUMMARY

According to an aspect of the present invention, there is provided a method of making zeolite microneedles that includes providing a polymer microneedles template, depositing zeolite seeds on the polymer microneedles template, and growing the zeolite seeds into an array of zeolite microneedles.

According to another aspect of the invention, where is provided a method of making hollow zeolite microneedles that includes providing a polymer microneedles template, depositing zeolite seeds on the polymer microneedles template, growing the zeolite seeds into an array of zeolite microneedles, and removing the polymer microneedles template from the zeolite microneedles.

According to a further aspect of the invention, there is provided zeolite microneedles that include a substrate layer and zeolites on the substrate layer to form an array of zeolite microneedles.

BRIEF DESCRIPTION OF THE DRAWINGS

FIG. 2 shows a fluorescent micrograph and schematic diagram of a tapered microneedles template.

FIG. 3 shows a fluorescent micrograph and schematic diagram of a bowl shaped microneedles template.

FIG. 4 shows a fluorescent micrograph and schematic diagram of a cylindrical microneedles template.

FIG. 5 shows the X-ray diffraction pattern of silicate-1 seeds with the characteristic zeolite peaks.

FIG. 6 shows a SEM image of 100 nm silicate-1 seeds well dispersed in solution.

FIG. 7 shows a SEM image of zeolite seeds-coated microneedles formed using an electrostatic method.

FIG. 8 shows a SEM image of open-tip zeolite microneedles with a shell thickness of about 1 μm.

FIG. 9 shows a SEM image of open-tip zeolite microneedles with a shell thickness of about 6 μm.

FIG. 10A shows a SEM image of closed-tip zeolite microneedles synthesized for about 24 hours.

FIG. 10B shows a SEM picture of open-tip zeolite microneedles synthesized for about 48 hours.

FIG. 11A shows FTIR results of a zeolite-coated polymer microneedles template before ozonation.

FIG. 11B shows FTIR results of a zeolite-coated polymer microneedles template after ozonation.

FIG. 12 shows a cell culture without the addition of zeolites.

FIG. 13A shows the cell culture of FIG. 12 within a day after the addition of zeolites.

FIG. 13B shows the cell culture of FIG. 12 one day after the addition of zeolites.

FIG. 13C shows the cell culture of FIG. 12 two days after the addition of zeolites.

FIG. 13D shows the cell culture of FIG. 12 three days after the addition of zeolites.

FIG. 14 shows a force-displacement graph of an insertion of zeolite microneedles into a skin's surface.

FIG. 15 shows an optical micrograph of microneedles after the insertion of FIG. 14.

FIG. 16A shows an optical micrograph of microneedles in a close-packed pattern.

FIG. 16B shows an optical micrograph of microneedles in a square pattern.

FIG. 17 shows a graph illustrating the effect of different wall thicknesses and packing geometries on the insertion force of microneedles.

FIG. 18 shows a force-displacement graph illustrating the strength of zeolite microneedles.

FIG. 19 shows a graph illustrating the force required to break zeolite microneedles at different wall thickness and packing geometries.

FIG. 20 shows a graph illustrating the change of concentration of sodium chloride in the lower chamber of a diffusion cell.

FIG. 21 shows microneedles as used in a pen applicator.

FIG. 22 depicts a cross-sectional view of the pen applicator of FIG. 21.

FIG. 23 depicts an electrical circuit of the pen applicator of FIG. 21.

FIG. 24 shows microneedles as used in a wristwatch applicator.

FIG. 25 shows an exploded view of FIG. 24.

DETAILED DESCRIPTION

Figure 1:
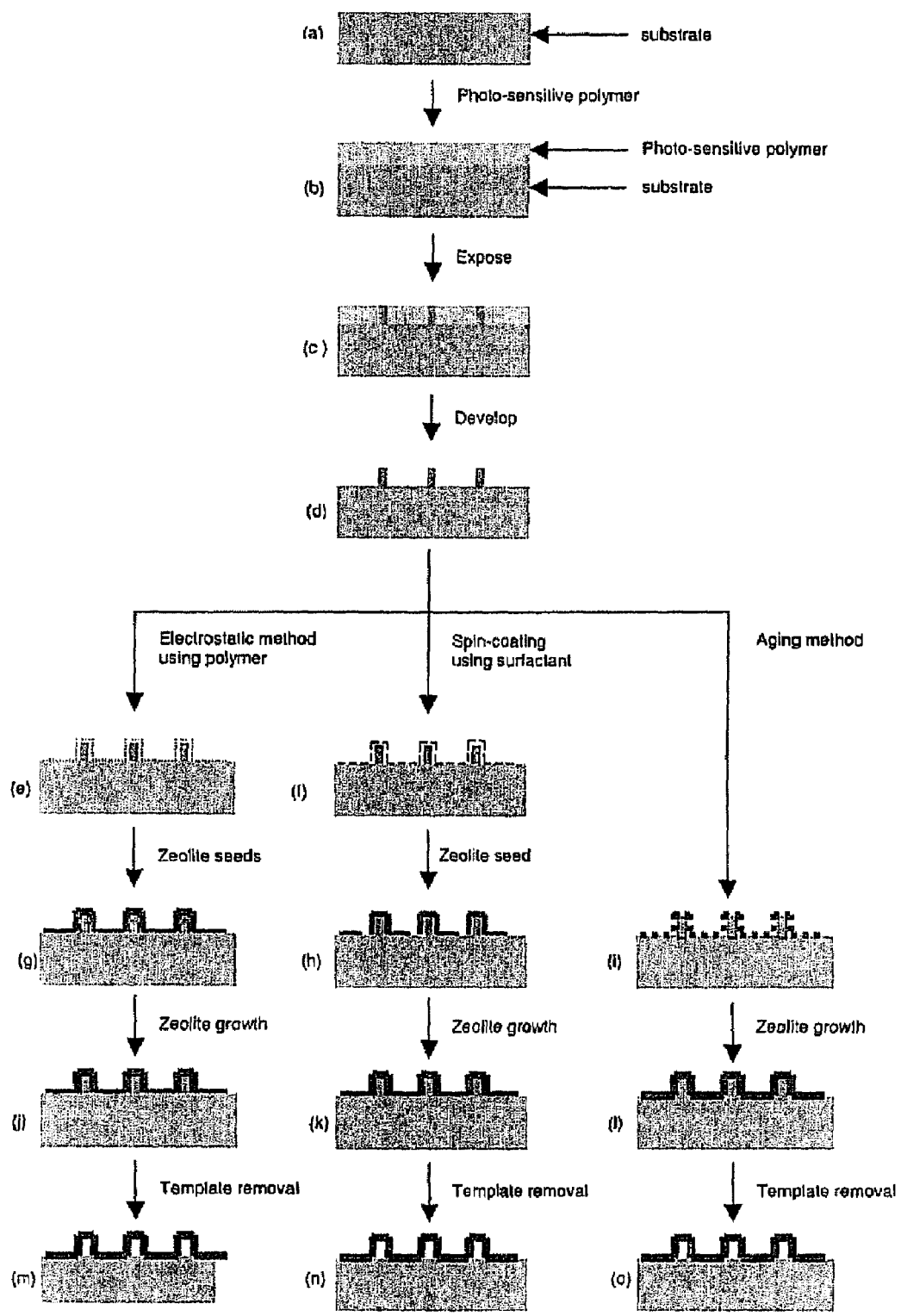
FIG. 1 depicts a schematic diagram illustrating a method of fabricating microneedles.

Reference will now be made in detail to the preferred embodiments of the invention, examples of which are also provided in the following description. Exemplary embodiments of the invention are described in detail, although it will be apparent to those skilled in the relevant art that some features that are not particularly important to an understanding of the invention may not be shown for the sake of clarity.

Furthermore, it should be understood that the invention is not limited to the precise embodiments described below and that various changes and modifications thereof may be effected by one skilled in the art without departing from the spirit or scope of the invention. For example, elements and/or features of different illustrative embodiments may be combined with each other and/or substituted for each other within the scope of this disclosure and appended claims.

A method of fabricating microneedles includes providing a polymer microneedles template, depositing zeolite seeds on the polymer microneedles template, growing the zeolite seeds into microneedles, and removing the polymer microneedles template, as shown in FIG. 1. Preferably, the microneedles are configured as an array, as depicted in FIGS. 10, 15 and 16.

The polymer microneedles template may be prepared using a photolithographic process. Microneedles with different degrees of tapering may be achieved by controlling the conditions for front exposure photolithography, for example, by varying the exposure time and/or developing time in the photolithographic process. The microneedles may contain either open-end tips or closed-end tips. The conformation of the tips may be controlled by varying the seeding methods and/or the growth conditions of the zeolite. Removing the polymer microneedles template can provide an array of hollow microneedles with a zeolite shell. The polymer microneedles template may be removed using an air calcination method or an ozonation method.

The polymer microneedles template be formed from a substrate layer and a photo-sensitive polymeric layer coated on the surface of the substrate layer. The photo-sensitive polymeric layer may include a material such as an SU-8 photoresist (SU-8 2075 made by MicroChem). The substrate layer may include silica, glass, quartz, metal, or any combination thereof. The polymer microneedles template may be prepared using a front exposure method by spin-coating the resist onto the surface of the substrate layer, for example, using a Solite 5110-C/PD Wafer Spinner (available from Solite). The resulting template precursor may then be pre-baked on a level hot plate and soft baked to evaporate the solvent. Coating fidelity and resist-substrate adhesion of the template can be improved by carrying out the soft baking step at a lower initial bake temperature, and allowing the solvent to be evaporated out of the polymer layer at a controlled manner.

The polymer microneedles template precursor may then be subjected to a photolithographic process. A mask may be aligned on the coated substrate and exposed to UV light, for example, using an AB-Manufacturing Contact Aligner (available from AB-Manufacturing). The photo-sensitive polymer is excited when exposed to UV light. For example, SU-8 has an optimal absorption of UV exposure from about 350 nm to about 400 nm. Exposure time may be used to control the shape of the polymer microneedles template and ultimately the shape of the microneedles. The exposure time may range from about 30 seconds to about 360 seconds. In one example, the template may be exposed to UV light for about 120 seconds. In another example, the template may be exposed to UV light for about 180 seconds. The longer the exposure time, the more the polymer may be excited. Following the exposure, a post-expose bake may be preformed to selectively cross-link the exposed area of the polymer layer. Thus, by varying the exposure time, photo-sensitive polymer layers with different extents of cross-linking may be prepared.

The unexposed portion of the photo-sensitive polymer may be removed by immersing the template precursor into a developer, for example, using a MicroChem's SU-8 Developer with agitation (available from MicroChem). The exposed area will form highly cross-linked polymers and will remain on the template, while the unexposed areas will be stripped out. Moreover, as with the exposure time, the developing time may also be used to control the shape of the polymer microneedles template and ultimately the shape of the microneedles. The developing time may range from about 3 minutes to about 90 minutes. In one example, the precursor may be immersed into the developer for 30 minutes. In another example, the precursor may be immersed into the developer for 60 minutes. The contact area between the polymer layer and the developer decreases at a high aspect ratio, and, thus, polymer microneedles templates with different tapered angles may be obtained by controlling the developing time. The longer the developing time, the more photo-sensitive polymer may be washed away.

Instead of the negative resist system described above, a positive resist system may be used to form the polymer microneedles template. For example, when a photo-sensitive polymer layer such as DNQ-Novolac is exposed to radiation, the polymer becomes soluble. Immersing the layer in a developer removes the exposed areas of the layer.

The microneedles fabricated on the polymer microneedles template may contain tapered angles of 75°, 90°, 100° or any other variations. A fluorescent microscope, such as a BX41 from Olympus, may be used to characterize the microneedles. FIG. 2 shows tapered microneedles with a height of about 280 µm, a top diameter of about 120 µm, a bottom diameter of about 240 µm, and a taper angle of 75°. FIG. 3 shows bowl shaped microneedles with a height of about 160 µm, a top diameter of about 200 µm, a bottom diameter of about 140 µm, and a taper angle of 1000. FIG. 4 shows cylindrical microneedles with a height of about 150 µm, a diameter of about 100 µm, and a taper angle of 90°. Consequently, by controlling the exposure and/or developing time, microneedles may be obtained in various shapes, including tapered, bowl and cylindrical shaped.

Microneedles may be prepared by electrostatically assembling, spin-coating or aging nanometer-sized zeolite nanocrystal seeds on the surface of the polymer microneedles template, and growing the zeolite seeds. Different zeolites may be grown by different zeolite seeds. For example, silicate-1 seeds may be used to grow MFI-type zeolites. Other zeolite-types may be prepared from the corresponding zeolite seeds, for example, LTA zeolite from NaA seeds. It may be possible to prepare other zeolite-types from seeds of a different zeolite. For example, FAU zeolite may be grown from NaA seeds. Zeolite seeds may be prepared by nucleation of zeolite nanocrystals from a homogeneous synthesis solution, followed by separation and purification. The seeds may then be stored as a suspension in solvents. It may also be possible to prepare zeolite seeds by grinding corresponding zeolite powder or by dissolution using acidic or basic solutions.

Zeolite nanocrystals may be made of crystalline molecular sieve materials or crystalline aluminosilicate materials. Zeolites belong to a broader material category known as "molecular sieves" and are often referred as such. Zeolites have uniform, molecular-sized pores, and can be separated based on their size, shape and polarity. For example, zeolites may have pore sizes ranging from about 0.3 nm to about 1 nm. The crystalline structure of zeolites may provide good mechanical properties and good thermal and chemical stability. Zeolites may be applied in chemical adsorption, separations and reactions, as well as in sensors and medical applications.

X-ray diffraction (XRD) analysis and scanning electron microscopy (SEM) may be carried out to determine the properties of zeolites, including their crystallinity, size and morphology. FIG. 5 shows an X-ray diffraction pattern of silicate-1 seeds obtained using an X-ray diffractometer (PANalytical, X'pert Pro). The pattern indicated that crystalline silicate-1 seeds were present. FIG. 6 shows a scanning electron micrograph of silicate-1 seeds obtained using a SEM (JEOL, JSM 6300). The micrograph indicated that the silicate-1 seeds were around 100 nm in size and well dispersed in solution.

Zeolites may be seeded on the polymer microneedles template using an electrostatic method. The attraction force between oppositely charged surfaces is the driving force for the electrostatic method. A layer of positively charged polyelectrolyte may be introduced into the polymer microneedles template. In one example, the template is immersed in a poly(diallyldimethylammonium chloride) PDADMAC (1 mg/ml in 0.5M NaCl, Sigma) polyelectrolyte solution. Zeolite seeds that are negatively charged may then be introduced and coated onto the positively charged surface of the polymer microneedles template. In another example, a negatively charged polyelectrolyte may be added onto the positively charged polyelectrolyte prior to the introduction of the zeolite seeds. An example of a negatively charged polyelectrolyte is polystyrene sulfonate (PSS), such as 1 mg ml$^-$ PSS in 0.5 M NaCl (Aldrich). A sequential adsorption of oppositely charged polyelectrolytes may be repeated one or more times, and then finished with an adsorption of a positively charged polyelectrolyte, to ensure the template is coated uniformly with positively charged polyelectrolyte. Zeolite seeds that are negatively charged may then be introduced and coated onto the positively charged surface. FIG. 7 shows a scanning electron micrograph of 100 nm zeolite seed-coated and tapered microneedles template formed using the electrostatic coating method, with the seeds uniformly coated on the template surface.

Zeolites may also be seeded onto the polymer microneedles template using a spin-coating method. A surfactant may first be spin-coated onto the polymer microneedles template, for example, by spin-coating (3-mercaptopropyl)trimethoxysilane (Aldrich, 95%) in ethanol (Merck, 99.9%) at more than 3000 rpm using a spin-coater (P-6000, Specialty Coating System, Inc.). Zeolite seed solution may then be similarly spin-coated onto the template. The surfactant and zeolite seed coating steps may be repeated one or more times. By controlling the speed of spin coating, the tip of the microneedle template can either be seeded or not seeded. For example, the speed of spin coating may vary from about 3000 rpm to about 6000 rpm. A completely seeded sample may grow a close-ended microneedle, whereas a microneedle having an unseeded tip may grow an open-ended microneedle. FIGS. 10A and 10B show electron micrographs of an array of microneedles formed using the spin-coating method, with close-ended tips and open-ended tips, respectively.

Zeolites may also be seeded onto the polymer microneedles template using an aging method. The polymer microneedles template may first be placed in a zeolite synthesis solution and allowed to age at low temperature. For example, the template may be placed into a zeolite synthesis solution containing 40 TEOS (Aldrich), 10 TPAOH (Aldrich) and 20000 DDI water by molar ratios for deposition of pure silica, silicate-1 zeolites.

After the zeolite seeds are deposited on the polymer microneedles template, the zeolite may be grown. The zeolite may be synthesized at high temperature, for example, in a Teflon bomb incubated at about 403 K for around 24 hours. A thin zeolite shell may subsequently grow on the seeded template and seed surface of the substrate. FIG. 8 shows a scanning electron micrograph of zeolite open-tip microneedles formed using the aging method, with a shell thickness of about 1 μm. Moreover, to increase the shell thickness, the zeolite microneedles may be transferred again into the zeolite synthesis solution containing 40 TEOS (Aldrich), 10 TPAOH (Aldrich) and 20000 DDI water by molar ratios to further grow for another 24 hours. FIG. 9 shows a scanning electron micrograph of zeolite open-tip microneedles formed using the aging method, with a shell thickness of about 6 μm.

Hollow microneedles may be obtained by removing the polymer microneedles template from the zeolite shell using an air calcination method or an ozonation method. In the air calcination method, the polymer microneedles template and the organic growth directing agent (or organic template) in the zeolite pores may be burnt off at a high temperature. In one example, the microneedles are calcined in an air-purged furnace that may be programmed to increase the temperature to about 873 K and kept for around 24 hours, at a rate of change to the temperature of about 0.5 K/min. FIGS. 10A and 10B show the scanning electron micrographs of closed-tip and open-tip zeolite microneedles, respectively, that have been calcined for 24 and 48 hours, respectively. After air calcination at about 873 K for around 24 hours, the polymer microneedles template have preferably been removed, and hollow zeolite microneedles remain.

In the ozonation method, the polymer microneedles template reacts with ozone to form gaseous byproducts in gas phase treatment, or soluble byproducts in liquid phase treatment. For example, the zeolite-coated template may be wrapped by heating tape (Thermolyne Briskheat) that may be controlled by a temperature controller (RKC) and a thermocouple (Omega, K-type). Pure oxygen or oxygen-ozone gas stream may then be fed and controlled by an ozone generator (Trailigas, Ozonconcept OZC 1002). The ozone treatment method is applicable in a gaseous phase as well as in a liquid phase.

Fourier Transform Infrared (FTIR) may be used to identify organic materials, and in some cases inorganic materials, using an infrared microscope (PerkinElmer, Spectrum GX). This technique measures the absorption of various infrared light wavelengths by the materials of interest. These infrared absorption bands can identify specific molecular components and structures. Referring to FIGS. 11A and 11B, the FTIR results show the zeolite-coated polymer microneedles template before and after ozonation, respectively. Three characteristic bands at wavenumbers of 2880 cm$^{-1}$, 2940 cm$^{-1}$ and 2980 cm$^{-1}$ were observed before ozonation, which indicated the presence of propyl groups with C—H stretching vibrations. After ozonation, however, those three peaks disappeared, which indicate the propyl groups might have been removed during ozone treatment.

Zeolite microneedles preferably are biocompatible. ISO 10993 describes a set of international standards that address the biological evaluation of medical devices. The basic biocompatibility tests include ISO 10993-1 and ISO 10993-5. The ISO 10993-1 test may be carried out to determine the characteristics and properties of zeolites, including their chemical, toxicological, physical, electrical, morphological, and mechanical properties. These can be determined by various characterization techniques such as SEM, XRD and FTIR, and are often available from the material safety data sheet (MSDS).

The ISO 10993-5 test may be carried out to determine the cytotoxicity of zeolites. In the elution test method, extracts may be obtained by placing the zeolites in cell culture media, for example, Madin-Darby Canine Kidney (MDCK) cells, under standard conditions. The cells will then be observed for visible signs of toxicity in response to the zeolites, such as a change in the size or appearance of cellular components, or a disruption in their configuration.

FIG. 12 shows an MDCK cell culture without the addition of zeolites, which was used as a control for the cytotoxicity test. FIGS. 13A, 13B, 13C and 13D show that the cells did not exhibit any changes in size or appearance from day 0, 1, 2 and 3, respectively, after the addition of Silicate-1 zeolites to the MDCK cell culture. As seen, the MDCK cells did not show visible signs of toxicity, because the numbers and configuration of the cell's monolayer appeared to be the same, thus indicating that Silicate-1 zeolites did not inhibit the growth or cause the death to the MDCK cells.

An insertion test may be performed to determine the force required for zeolite microneedles to penetrate a skin's surface. FIG. 14 shows a force-displacement graph for the insertion of the zeolite microneedles into a pig's skin. The graph can be divided into three stages. In stage A, the horizontal line represented when the microneedles sample started to move towards the skin at a constant speed, which indicated that little force was required to overcome the resistance of air between the microneedles and the skin, for a small displacement. In stage B, the increasing slope represented when the microneedles began to make contact with the skin, and the skin deformed under pressure. As the microneedles insertion is resisted by the stratum corneum of the skin, a greater force is therefore required for the penetration. In stage C, a small decrease in the force exerted represented when the microneedles were inserted into the skin, and the discontinuity between stages B and C indicated the occurrence of insertion. Since the inner part of the skin is less resistive than the outer stratum corneum, less force is required for further penetration.

The effects of the wall thickness and the packing geometries of the open-tip zeolite microneedles on the force of insertion may also be studied. FIGS. 16A and 16B show the optical micrographs of an array of microneedles of a close-packed pattern and a squared pattern, respectively. FIG. 17 shows a graph illustrating the insertion force for different thicknesses of zeolite wall and different packing geometries of microneedles. As seen, the insertion force between the square and close-packed patterns was similar at a given zeolite wall thickness. The insertion force to insert through a pig's skin increased with thicker zeolite wall, which indicated that a thicker wall was less sharp.

A strength test may be performed to determine the force required to break the zeolite microneedles. For example, a strength test may be performed using a movable load cell of a Compressive/Tensile Tester (Instron, model 5567). FIG. 18 shows a force-displacement graph for the strength test. The graph can be divided into three stages. In stage A, the horizontal line represented when the microneedles sample started to move towards the tester platform at a constant speed, which indicated that little force was required to overcome the resistance of air between the microneedles and the skin for a small displacement. In stage B, an increasing slope represented when the microneedles began to make contact with the tester platform, because a greater force was required to move further downward. In stage C, the discontinuity represented when one of the microneedles broke. The further increase in slope indicated larger force was required for additional displacement, since the microneedles were pressed against the test platform.

The effects of the wall thickness and the packing geometries of the open-tip zeolite microneedles on the breakage force may also be studied. FIG. 15 shows an optical micrograph of an array of zeolite microneedles after the insertion into skin. As shown, over 90% of the needles remained intact after the insertion, which proves that zeolite microneedles can have the mechanical strength for drug delivery. FIG. 19 shows a graph illustrating the breakage force for different thicknesses of zeolite walls and different packing geometries of microneedles. As seen, the breakage force between the square and close-packed patterns was similar at a given zeolite wall thickness. The breakage force increases with thicker zeolite wall, which indicates that a thicker wall is stronger.

A drug delivery test may be performed to determine the diffusion rate of drug through a membrane, for example, using a diffusion cell consisted of an upper chamber and a lower chamber separated by a membrane. FIG. 20 shows the change of the concentration of sodium chloride in the lower chamber of the diffusion cell. The "test" graph represents when membrane was pierced while "control" graph represents when the membrane was not pierced. The results show that the concentration of sodium chloride in saline solution in the lower chamber increases with time at a constant rate when the membrane was pierced, but the concentration remained unchanged when the membrane was not pierced.

Zeolite microneedles may be applied in medical applications including drug delivery and body fluid extraction. Drug delivery may include vaccination, hormone regulation and insulin delivery. Moreover, the microneedles may be used in drug delivery applicators, such as pen applicators or wristwatch applicators. Body fluid extraction may cover blood glucose analysis and building sensors. Apart from the use of drug delivery, the microneedles can serve as body fluid extractor and/or biosensor. It is possible to use microneedles to draw blood samples for analysis with an onboard sensor. This data can then be processed to calculate the required medicinal dosage. The microneedles may be used in cosmetics, such as creating cosmetic facial masks or tattoos.

Zeolite microneedles may be used in a reusable pen applicator 10, as depicted in FIG. 21. The pen applicator 10 may include a protective case 12, a reservoir 14, a control system 16 and a battery 18. The protective case 12 may serve to protect the microneedles 20 when the microneedles 20 are not in use, and may ensure vertical insertion of the microneedles 20 at a constant force to reduce the breakage during use. The reservoir 14 may be used for drug storage. The control system 16 may include a motor 22 and a control circuitry 24. The pen applicator 10 may be driven by the motor 22 controlled by the control circuitry 24 to ensure precise rate of injection and drug dosage. The microneedles 20 may be replaced after use, and thus the pen applicator 10 may be reusable.

FIG. 22 shows a schematic illustrating the mechanism of the pen applicator 10 responsible for the drug injection and loading. The mechanism may include a screw 26, a plug 28, a motor 30 and a gearbox 32. The plug 28 may be attached to the end of the screw 26 to be driven by the motor 30. The gearbox 32 may be attached to the motor 30 to decrease the rotation speed and to increase the torque to the plug 28. The plug 28 may be moved forward to inject drugs and may be moved backward to load drugs.

FIG. 23 shows a schematic illustrating the electronic circuit 34 of the pen applicator 10 responsible for controlling the current flowing through the motor 30 that drives the drug injection and loading. The circuit 34 may control the motor 30, the directions of rotation, and one or more external indictor lights (LED) 36. The circuit 34 may include a switch 38 and a power source made of one of more batteries 40.

The zeolite microneedles may also be used in a programmable wristwatch applicator 50, as depicted in FIGS. 24 and 25. The wristwatch applicator 50 may include a liquid crystal display (LCD) 52, a micro-pumping system 54, a microprocessor 56, a drug storage chamber 58, rotating tracks of microneedles 60 and a battery 62.

The wristwatch applicator 50 may be programmed to inject the required dosage of drugs into a human body at a preset time. The drugs may be pumped from the drug storage chamber 58 through the microneedles into the human body using the micro-pumping system 54. Examples of micro-pumping systems include lead zirconate titanate or piezoelectric ceramic (PZT) and magnetic membrane micropumps. The microprocessor 56 may allow users to adjust the rate of drug injection, the dosage of drugs and the desired timing of injection, each of which may be displayed on the LCD screen 52. The users may find the wristwatch applicator 50 convenient to use because the rotating track 60 of microneedles may rotate after each injection; therefore, replacement of microneedles after each use may not be necessary, and the drug may be refilled in the drug storage chamber 58.

The microneedles are further illustrated by the following examples, which are not to be construed in any way as imposing limitations upon the scope thereof. On the contrary, it is to be clearly understood that resort may be had thereof which, after reading the description herein, may suggest themselves to those skilled in the art without departing from the spirit of the specification and/or the scope of the appended claims.

EXAMPLES

Example 1

Preparation of SU-8 Tapered Microneedle Template (75°)

The first step included spin-coating 1 ml of SU-8 resist on the surface of a substrate (e.g. silica, glass, quartz and metal) at an acceleration of around 300 rpm and holding at around 1000 rpm for a total of about 30 seconds using a Solite 5110-C/PD Wafer Spinner. The second step included pre-baking the SU-8 resist at 338K for 10 minutes and then soft baking it at around 368K for about 30 minutes. The third step included cooling the SU-8 resist down to room temperature. The fourth step included aligning a pattern mask on the SU-8 coated substrate and exposed it to UV light for about 180 seconds using an AB-Manufacturing Contact Aligner. The fifth step included post-baking the resist on a level hot plate at around 368K for about 30 minutes. The sixth step included cooling the resist down to room temperature. The seventh step included developing the SU-8 coated substrate using a Micro-Chem's SU-8 Developer for about 30 minutes with agitation.

Characterization

The polymer microneedles template was characterized using a fluorescent microscope. The sample was cross-sectioned and cleaned with DDI water to remove dirt and contaminants. The sectioned sample was then mounted on a microscopic slide using adhesives tapes. The cross-section sample was subsequently examined under a fluorescent microscope (BX41, Olympus). The light shutter was fully opened during the operation and the excitation wavelength of light source was around 450-490 nm. FIG. 2 shows tapered microneedles with about 280 μm in height, top diameter of about 120 μm, bottom diameter of about 240 μm, and a taper angle of 75°.

Example 2

Preparation of SU-8 Bowl Shaped Microneedle Template (100°)

The first step included spin-coating 1 ml of SU-8 resist on the surface of a substrate (e.g. silica, glass, quartz and metal) at an acceleration of around 300 rpm and hold at around 2000 rpm for a total of about 30 seconds using a Solite 5110-C/PD Wafer Spinner. The second step included pre-baking the resist on a level hot plate at around 338K for about 10 minutes and then soft-baking it at around 368K for about 30 minutes. The third step included cooling the SU-8 resist down to room temperature. The fourth step included aligning the pattern mask on the SU-8 coated quartz substrate and exposed it to UV light for about 120 seconds using an AB-Manufacturing Contact Aligner.

The fifth step included post-baking the resist on a level hot plate at around 368K for about 30 minutes. The sixth step included cooling the resist down to room temperature. The seventh step included developing the SU-8 coated substrate using a MicroChem's SU-8 Developer for about 30 minutes with agitation. The polymer microneedles template was characterized using a fluorescent microscope as described in Example 1. FIG. 3 shows bowl shaped microneedles with about 160 μm in height, top diameter of about 200 μm, bottom diameter of about 140 μm, and a taper angle of 100°.

Example 3

Preparation of SU-8 Cylinder Microneedle Template (90°)

The first step included spin-coating 1 ml of SU-8 resist on the surface of a substrate (e.g. silica, glass, quartz and metal) at an acceleration of around 300 rpm and hold at around 2000 rpm for a total of about 30 seconds using a Solite 5110-C/PD Wafer Spinner. The second step included pre-baking the SU-8 resist on a level hot plate at around 338K for about 10 minutes and then soft-baking it at around 368K for about 30 minutes. The third step included cooling the resist down to room temperature. The fourth step included aligning the pattern mask on the SU-8 coated quartz substrate and exposed it to UV light for about 180 seconds using an AB-Manufacturing Contact Aligner.

The fifth step included post-baking the resist on a level hot plate at around 368K for about 30 minutes. The sixth step included cooling the resist down to room temperature. The seventh step included developing the SU-8 coated quartz substrate using a MicroChem's SU-8 Developer for about 60 minutes with agitation. The polymer microneedles template may be characterized using a fluorescent microscope as described in Example 1. FIG. 4 shows cylindrical microneedles with about 150 μm in height, a diameter in size of about 100 μm, and a taper angle of 90°.

Example 4

Preparation of Silicalite-1 (Sil-1) Seed Solution

The first step included placing and stirring 60 ml of 1.0 M tetrapropylammonium hydroxide (TPAOH, Aldrich) in a cleaned Teflon container. The second step included adding 0.9 g of sodium hydroxide (NaOH, BDH, 99%) slowly into the stirring TPAOH solution. The third step included keeping the solution at around 353K in a water bath.

The fourth step included slowing adding and dissolving 15 g of fumed silica (Aldrich, 99.8%) into the stirring solution. The fourth step included stirring the solution mixture for about 24 hours at ambient conditions to obtain a clear and homogeneous synthesis solution.

The fifth step included placing a Teflon container that contained the synthesis solution in a stainless steel autoclave. The sixth step included placing the autoclave in a pre-heated oven at around 403 K for about 8 hours hydrothermal treatment. The seventh step included cooling the synthesis down to quench the crystallization by compressed air. The eight step included centrifuging the synthesis solution at $\geq 2000$ rpm by a high speed centrifuge (Sorvall RC 5C Plus) for about 15 minutes to remove any coarse particles. The ninth step included centrifuging the recovered solution at $\geq 2000$ rpm for about 20 minutes to obtain the seeds at the bottom of the centrifuge. The tenth step included removing the solution and adding ethanol (Merck, 99.9%) to re-suspend the seeds. Steps ninth and tenth were repeated until the solution was neutral, i.e. at around pH 7.

Seed Characterization

The seed solution was characterized using an X-Ray Diffraction (XRD). The sample was carefully packed in an aluminum holder, and the holder was clamped on the X-Ray diffractometer (PANalytical, X'pert Pro). The sample was then exposed to X-Ray with wavelength of 1.54 Å generated from copper source. The sample clamp and the X-ray source were rotated at the angular speed of about 0.0087 (rad/s). The crystallinity of the prepared sample was then examined using the XRD graph. FIG. 5 shows an X-ray diffraction pattern of silicate-1 seed using an X-ray diffractometer (PANalytical, X'pert Pro), which indicates that crystalline silicate-1 seeds were obtained.

Characterization

The seeds were also characterized using a Scanning Electron Microscopy (SEM). The zeolite seeds were first mounted on copper sample holder using conducting adhesives and silver paste before sputter-coating (Denton, DESK II) 20 nm of gold. SEM (JEOL, JSM 6300) images were then taken to provide information on the film morphology and crystal grain size. FIG. 6 shows a scanning electron micrograph of silicate-1 seeds using a SEM (JEOL, JSM 6300), which indicates silicate-1 seeds that were around 100 nm in size and were well dispersed in solution.

Example 5

Zeolite Seeding on SU-8 Polymer Microneedles Template by Electrostatic Method The first step included immersing the SU-8 polymer microneedles template in 5 ml of Poly(diallyldimethylammonium chloride) PDADMAC (1 mg/ml in 0.5M NaCl, Sigma) polyelectrolyte solution. The second step included stirring the solution at room temperature about 15 minutes to allow the adsorption of the positively charged polyelectrolyte. The third step included washing the coated SU-8 polymer microneedles template three times with 0.5 M NaCl to remove the excess PDADMAC polyelectrolyte. The fourth step included adding 5 ml aliquot of a negatively charged polyelectrolyte (polystyrene sulfonate) PSS (1 mg ml$^{-1}$ in 0.5 M NaCl, Aldrich) to form a second polyelectrolyte layer with a negative charge on the SU-8 polymer microneedles template surface.

The fifth step included washing the coated SU-8 polymer microneedles template three times with 0.5 M NaCl to remove the excess PSS polyelectrolyte. The sequential adsorption of oppositely charged polyelectrolyte was repeated three times to obtain a uniform positive surface charge on the SU-8 polymer microneedles template, herein referred to as SU-8/(PDADMAC/PSS/PDADMAC). The sixth step included re-suspending the positively charged SU-8 polymer microneedles template in zeolite seed (0.2 wt %) solution. The seventh step included stirring the suspension at room temperature overnight.

Characterizations

The zeolite seeds coated SU-8 polymer microneedles template was first cleaned with DDI water to remove dirt and contaminants. The zeolite seeds coated SU-8 polymer microneedles template was then mounted on copper sample holder using conducting adhesives and silver paste before sputter-coating (Denton, DESK II) 20 nm of gold. The samples were imaged at high magnification with a SEM (JEOL, JSM 6300). FIG. 7 shows a scanning electron micrograph of 100 nm zeolite seeds coated polymer tapered microneedles template using the electrostatic coating method, which indicates that the seeds were uniformly coated on the template surface.

Example 6

Zeolite Seeding on SU-8 Polymer Microneedles Template by Spin Coating Method The first step included cleaning the SU-8 polymer microneedles template with ethanol (Merck, 99.9%) and distilled deionized water and drying it in an oven at around 338 K. The second step included spin-coating 0.05 M of (3-mercaptopropyl)trimethoxysilane (Aldrich, 95%) in ethanol (Merck, 99.9%) on the SU-8 polymer microneedles template at $\geq 3000$ rpm using a spin-coater (P-6000, Specialty coating system, Inc.). The third step included preparing a 0.5 wt. % seed solution as descried in Example 4, and spin-coating it at $\geq 3000$ rpm with the spin-coater. The fourth step included drying the seed-coated template in an oven at around 338 K for about 10 minutes. The second and fourth steps were repeated three times.

Example 7

Preparation of Zeolite Microneedles—Thin Shell Wall

The first step included transferring zeolite seed coated SU-8 polymer microneedles template into a zeolite synthesis solution containing 40 TEOS (Aldrich), 10 TPAOH (Aldrich), and 20000 DDI water by molar ratios for deposition of pure silica, silicate-1 zeolites. The second step includes carrying out the synthesis in a Teflon bomb and incubating it at around 403K for about 24 hours. The third step includes growing a thin zeolite shell on the seeded polymer microneedles templates and the seed surface of the substrate. The fourth step included washing away the zeolite particles deposited from the solutions using DDI water. The thin zeolite shell wall was characterized using a SEM as described in Example 4. FIG. 8 shows a scanning electron micrograph of zeolite open-tip microneedles with a shell thickness of about 1 μm.

Example 8

Preparation of Zeolite Microneedles—Thick Shell Wall

The first step included transferring zeolite seed coated SU-8 polymer microneedles template into a zeolite synthesis solution containing 40 TEOS (Aldrich), 10 TPAOH (Aldrich), and 20000 DDI water by molar ratios for deposition of pure silica, silicate-1 zeolites. The second step includes carrying out the synthesis in a Teflon bomb and incubating it at around 403K for about 24 hours. The third step includes growing a thin zeolite shell on the seeded polymer microneedles templates and the seed surface of the substrate. The fourth step included washing away the zeolite particles deposited from the solutions using DDI water. The fifth step included transferring Zeolite microneedles into the zeolite synthesis solution again to further grow for another 24 hours. The sixth step included washing away the zeolite particles deposited from the solutions using DDI water. The thick zeolite shell wall was characterized using a SEM as described in Example 4. FIG. 9 shows a scanning electron micrograph of zeolite open-tip microneedles with a shell thickness of about 6 μm.

Example 9

Preparation of Zeolite Microneedles—Aging Method

The first step included immersing the SU-8 polymer microneedles template into a zeolite synthesis solution containing 40 TEOS (Aldrich), 10 TPAOH (Aldrich), 20000 DDI water by molar ratios for deposition of pure silica, silicate-1 zeolites at around 298K for about 24 hours. The second step included carrying out the synthesis in a Teflon bomb and incubating at around 403K for about 24 hours. The third step includes growing a thin zeolite shell on the seeded polymer microneedles templates and the seed surface of the substrate. The fourth step included washing away the zeolite particles deposited from the solutions using DDI water.

Example 10

Removal of SU-8 Polymer Microneedles Template—Air Calcinations

The SU-8 polymer microneedles template was removed by air calcination. The first step included putting the zeolite-coated polymer microneedles template in a crucible that can withstand high temperature treatment. The second step included putting the crucible into an air-purging furnace. The furnace was programmed to increase the temperature to around 873K and kept it for about 24 hours. The rate of change of the temperature was 0.5 K/min. The zeolite microneedles was characterized using a SEM as described in Example 4. FIGS. 10A and 10B show the scanning electron micrographs of an array of closed-tip and open-tip zeolite microneedles, respectively, that had been synthesized for 24 and 48 hours, respectively.

Example 11

Removal of SU-8 Polymer Microneedles Template—Ozonation

The SU-8 polymer microneedles template was removed by ozonation. The first step included placing zeolite-coated polymer microneedles template in a stainless steel housing in which rubber and graphite o-rings were used to provide a leak-free system for gas flow through the cabinet. The stainless steel consisted of inlet and outlet for retentate to flow through the tube. The second step included wrapping the step up with heating tape (Thermolyne Briskheat) that was controlled by temperature controller (RKC) and thermocouple (Omega, K-type). The third step included increasing the temperature of the vessel to around 473K with temperature increasing rate of about 0.5 K/min.

The fourth step included feeding pure oxygen or oxygen-ozone gas stream to the unit at a constant flow rate of about 250 cm$^3$/min when the temperature reached around 473K. The ozone concentration could be controlled by adjusting the power of the ozone generator (Trailigas, Ozonconcept OZC 1002). The fifth step included keeping the gas pressure inside the tube at about 1.2 bars during the ozone treatment. The sixth step included cooling the setup down at the rate of about 0.5 K/min to room temperature after ozone treatment. FIGS. 11A and 11B, the FTIR results show the zeolite-coated polymer microneedles template before and after ozonation, respectively.

Characterization

The SU-8 polymer microneedles template was characterized using Fourier Transform Infrared (FTIR). The first step included mounting a zeolite-coated polymer microneedles template before ozonation on the sample stage of the infrared microscope (PerkinElmer, Spectrum GX). The second step included flowing dry air (without moisture and carbon dioxide) through during the measurement. The third step included focusing the sample by the microscope in visible light mode. The fourth step included changing the light source to IR mode and adjusting the area for analysis to be 100 μm×100 μm square after focusing.

The fifth step included scanning the signal of the IR from the sample. The sixth step included treating the zeolite-coated polymer microneedles template in ozone for 30 minutes to about 4 hours. The seventh step including mounting the sample on a cell and placing it under the infrared microscope for analysis. The eighth step included focusing the sample by the microscope in visible light mode. The ninth step included changing the light source to IR mode after focusing. The tenth step included scanning the signal of the IR from the sample.

Example 12

Evaluation of Zeolite Microneedles on its Biocompatibility

The first step included preparing zeolite fluid extract by adding 1 g of Silicate-1 crystal in 10 ml culture medium at about 310 K. The second step included deriving Madin- Darby Canine Kidney (MDCK) cells from normal dog's kidney as the cultured-cell monolayer. The third step included applying the fluid extract obtained to a cultured-cell monolayer replacing the medium that had nourished the cells. The fourth step included incubating the cultures at about 310 K and periodically removing for microscopic examination at designated times for as long as 3 days. FIG. 12 shows the cell culture without the addition of zeolite, which was used as a control for the cytotoxicity test. FIGS. 13A, 13B, 13C and 13D show that the cells did not exhibit any changes in size or appearance from day 0, 1, 2 and 3, respectively, after the addition of Silicate-1 zeolites to the MDCK cell culture.

Example 13

Insertion Test

Insertion test was operated using a proprietary software (Merlin). The first step included attaching the microneedles sample to a movable load cell with maximum load of 100 N of the Compressive/Tensile Tester (Instron, model 5567). The second step included placing a pig's skin on an agar plate beneath the microneedles. The third step included moving the microneedles towards the skin at a constant velocity of 1.1 mm/s by the program. The fourth step included identifying the insertion sample into the skin when the force exerted by the load suddenly dropped. The fifth step included using an optical microscope (Olympus BX41) to examine the sample after the test.

FIG. 14 shows a force-displacement graph for the insertion of the zeolite microneedles into the pig's skin. FIG. 16 shows the optical micrographs of an array of microneedles with a close-packed pattern and a square pattern, respectively.

Example 14

Strength Test

Insertion test was operated using a proprietary software (Merlin). The first step includes attaching the microneedles sample to a movable load cell with maximum load of 100 N of the Compressive/Tensile Tester (Instron, model 5567). The second step included moving the microneedles towards the skin at a constant velocity of 1.1 mm/s by the program. The fourth step included identifying the needle breakage when the force exerted by the load suddenly increased significantly. The fifth step included using an optical microscope (Olympus BX41) to examine the sample after the test. The sixth step included calculating safety ratio to determine the likeliness of needle breakage throughout the insertion, which is defined as the amount of breakage force per unit of insertion force.

FIG. 18 shows a force-displacement graph for the strength test. FIG. 15 shows the optical micrograph of an array of zeolite microneedles after insertion test. As shown, over 90% of the needles remained intact after the insertion, which proves that zeolite microneedles have the mechanical strength for drug delivery. Table 1 summarizes the safety ratio of zeolite microneedles sample with different thicknesses. A larger safety ratio indicates safer microneedles. The results prove that zeolite microneedles are stronger than the polymeric microneedles and approaches nickel microneedles in strength.

TABLE 1

Insertion force, breakage force and safety ratio for zeolite microneedles with different thicknesses

| Wall thickness | Insertion Force | Breakage Force | Safety Ratio |
| --- | --- | --- | --- |
| 2.5 µm | 0.015 N | 0.0683 N | 4.5533 |
| 4.8 µm | 0.023 N | 0.0971 N | 4.2217 |
| 6.4 µm | 0.031 N | 0.1259 N | 4.0613 |

Example 15

Evaluation of Diffusivity of Zeolite Microneedles

Drug delivery test was performed to investigate the diffusion rate of drug through a membrane. The diffusion cell consisted of an upper chamber and a lower chamber separated by a membrane.

The first step included placing a physiological saline solution (1.2 wt % sodium chloride) in an upper chamber of a diffusion cell. The second step included using a layer of artificial skin, e.g. pig's skin, as the membrane of the diffusion cell. The third step included piercing the skin with the microneedles samples and placing them in the diffusion cell. The fourth step included placing DDI water in a lower chamber of the diffusion cell with continuous stirring. The fifth step included putting a conductivity meter probe in the lower chamber and measuring the conductivity in real time. The sixth step included recording the conductivity reading at a fixed time interval and using the calibration data to convert it to concentration units.

FIG. 20 shows a graph illustrating the change of the concentration of sodium chloride in the lower chamber of the diffusion cell. The lower graph depicted the control, which represented the un-pierced pig's skin. The upper graph depicted the test results, which represented the pierced pig's skin. As shown, the concentration of sodium chloride remained unchanged with time with the un-pierced sample. On the other hand, the concentration of sodium chloride increased steadily with time with the pierced sample, which indicated that the physiological saline solution diffused across the membrane of the diffusion cell from the upper chamber and into the lower chamber. Consequently, the result indicates zeolite microneedles may be used in drug delivery.

While the examples of the zeolite microneedles have been described, it should be understood that the zeolite microneedles are not so limited and modifications may be made. The scope of the zeolite microneedles is defined by the appended claims, and all devices that come within the meaning of the claims, either literally or by equivalence, are intended to be embraced therein.

We claim:
1. A method of making zeolite microneedles, comprising:
   providing a polymer microneedles template;
   depositing zeolite seeds on said polymer microneedles template; and
   growing said zeolite seeds into an array of zeolite microneedles.
2. The method of claim 1, wherein said providing comprises exposing a photo-sensitive polymer to ultraviolet light.
3. The method of claim 2, wherein said providing further comprises immersing said photo-sensitive polymer into a developer.
4. The method of claim 1, wherein said depositing comprises electrostatically assembling zeolite seeds.

5. The method of claim 4, wherein said assembling comprises introducing a positively charged polyelectrolyte into said template.

6. The method of claim 5, wherein said positively charged polyelectrolyte comprises poly(diallyldimethylammonium chloride).

7. The method of claim 5, wherein said assembling further comprises introducing negatively charged zeolite seeds onto said positively charged polyelectrolyte.

8. The method of claim 5, wherein said assembling further comprises introducing a negatively charged polyelectrolyte onto said positively charged polyelectrolyte.

9. The method of claim 8, wherein said negatively charged polyelectrolyte comprises polyelectrolyte (polystyrene sulfonate) PSS.

10. The method of claim 1, wherein said depositing comprises spin-coating zeolite seeds on said template.

11. The method of claim 10, wherein said zeolite seeds comprise silicate-1 seeds.

12. The method of claim 1, wherein said depositing comprises aging zeolite seeds on said template.

13. The method of claim 1, wherein said growing comprises incubating the zeolite seeds at about 403K for around 24 hours.

14. The method of claim 1, further comprising removing said polymer microneedles template from said zeolite microneedles.

15. The method of claim 14, wherein said template is removed using an air calcination method.

16. The method of claim 14, wherein said template is removed using an ozonation method.

17. Zeolite microneedles, comprising:
a substrate layer; and
zeolites on said substrate layer to form an array of zeolite microneedles.

18. The zeolite microneedles of claim 17, wherein said zeolite microneedles have a taper angle from about 75° to about 100°.

19. The zeolite microneedles of claim 17, wherein said substrate layer comprises silica, glass, quartz, metal or any combination thereof.

20. The zeolite microneedles of claim 17, wherein said zeolite microneedles comprise close-ended tips.

21. The zeolite microneedles of claim 17, wherein said zeolite microneedles comprise open-ended tips.

22. The zeolite microneedles of claim 17, wherein said zeolite microneedles are hollow.

23. The zeolite microneedles of claim 17, wherein said zeolite microneedles are biocompatible.

24. A pen applicator, comprising a control system and the zeolite microneedles of claim 17 attached to said control system.

25. A wristwatch applicator, comprising a microprocessor and the zeolite microneedles of claim 17 attached to said microprocessor.

* * * * *